United States Patent [19]

Duffett

[11] Patent Number: Plant 5,323

[45] Date of Patent: Nov. 6, 1984

[54] CHRYSANTHEMUM PLANT NAMED YELLOW NOVA

[75] Inventor: William E. Duffett, Salinas, Calif.

[73] Assignee: Yoder Brothers, Inc., Barberton, Ohio

[21] Appl. No.: 419,008

[22] Filed: Sep. 16, 1982

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Yellow Nova characterized by its flat capitulum form; daisy capitulum type; yellow ray floret color; diameter across face of capitulum ranging from 75 to 95 mm. at maturity; uniform nine (9) week photoperiodic flowering response to short days; tall plant height when grown as a single stem cut spray; 10 to 15 cm. peduncles on open, normally terminal sprays, and slow development of tight green discs; tolerance of 13°C. (56° F.) for initiation and development when grown in single stem cut spray programs with a continuous dark period of 13 to 15 hours.

3 Drawing Figures

The present invention comprises a new and distinct cultivar of *Chrysanthemum morifolium*, Ramat., hereinafter referred to by the cultivar name Yellow Nova.

Yellow Nova is an induced mutation of an unnamed light bronze daisy, which was in turn an induced mutation derived from the pink daisy Nova disclosed in U.S. Plant Pat. No. 4,992. The unnamed light bronze daisy parent was irradiated and reselected to clarify its color by the removal of undesirable light bronze tinging.

The parental mutation of Yellow Nova was a product of a planned mutation induction program which had the objective of creating a new chrysanthemum cultivar for cut spray mum programs with daisy capitulum type, yellow ray floret color, nine (9) week flowering response, and having the ability to produce commercially acceptable quality in year round programs. Yellow color was required to compliment the original pink color of Nova and retain all other traits.

Yellow Nova was discovered and selected as one flowering plant within a population of plants propagated from stock plants which had been irradiated as cuttings with an X-ray source of 900 rads by William E. Duffett on Apr. 26, 1980 in a controlled environment in Salinas, Calif.

The first act of asexual reproduction of Yellow Nova was accomplished when vegetative cuttings were taken from the initial selection on July 26, 1980 in a controlled environment in Salinas, Calif. by a technician working under formulations established and supervised by William E. Duffett.

Horticultural examination of selected units initiated June, 1981 had demonstrated that the combination of characteristics as herein disclosed for Yellow Nova are firmly fixed and are retained through successive generations of asexual reproduction.

Yellow Nova has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Yellow Nova which in combination distinguish this chrysanthemum as a new and distinct cultivar:

(1) flat capitulum form;

(2) daisy capitulum type;

(3) yellow ray floret color with minimum color oxidation;

(4) yellow-green (immature) to yellow (mature) disc floret color;

(5) diameter across face of capitulum ranging from 75 to 90 mm. at maturity;

(6) uniform nine (9) week photoperiodic flowering response to short days;

(7) medium peduncle length, ranging from 10 to 15 cm.;

(8) tall plant height (requiring one to two long day weeks prior to short days to attain a flowered plant height of 80 to 90 cm. for May through October flowerings); and (9) low temperature tolerance of 13° C. (56° F.) for initiation and development when grown in single stem cut spray programs with a continuous dark period of 13 to 15 hours.

The accompanying photographic drawings show typical inflorescence and foliage characteristics of Yellow Nova, with the colors being as nearly true as possible with illustrations of this type. Sheet 1 is a color photograph of Yellow Nova grown as a single stem cut spray. Sheet 2 is a black and white photograph showing the foliage of Yellow Nova at three stages of growth. Sheet 3 is a black and white photograph of three views of the inflorescence of Yellow Nova.

Of the many commercial cultivars known to the present inventor, the most similar in comparison to Yellow Nova is Florida Marble (U.S. Plant Pat. No. 3,288). Reference is made to attached Chart A which compares certain characteristics of Yellow Nova to those same characteristics of Florida Marble.

In comparison to Florida Marble, Yellow Nova has deeper ray floret color, with superior color retention and a slower rate of oxidation; its spray formation is generally terminal with a shorter peduncle length and taller plant height; it has a smaller diameter across the face of the capitulum up to 15 mm.; the capitulum form, capitulum type and flowering response to short days are similar.

In the following description, color references are made to The Royal Horitcultural Society Colour Chart. The color values were determined between 11:00 and 11:15 A.M. Aug. 10, 1982 under 150 foot-candle light intensity.

CLASSIFICATION

Botanical: *Chrysanthemum morifolium,* Ramat., cv Yellow Nova.

Commercial: Cut single spray.

INFLORESCENCE

Capitulum:

*Form.*—Flat.

*Type.*—Single or daisy.

*Diameter across face.*—75 To 90 mm.

Corolla of ray florets:

*Color (general tonality from a distance of three meters).*—Yellow.

*Color (abaxial).*—5A Oxidizing to 5C.

*Color (adaxial).*—5B Oxidizing to 5C.

*Shape.*—Oblong, rounded tip.

Corolla of disc florets:

*Color (mature).*—7B.

*Color (immature).*—145A.

Reproductive organs:

*Androecium.*—Present disc florets only; scant pollen.

*Gynoecium.*—Present both ray and disc florets.

PLANT

General appearance:

*Height.*—Tall, 75 to 90 cm., as a flowering plant from a rooted cutting, with no long days for April through November flowerings and maintaining a minimum nightly 13 hour continuous dark period.

Foliage:

*Color (abaxial).*—147A.

*Color (adaxial).*—147B.

*Shape.*—Deeply lobed and serrated.

CHART A

COMPARISON OF YELLOW NOVA AND FLORIDA MARBLE

| CULTIVAR | RAY FLORET COLOR | CAPITULUM FORM AND TYPE | SPRAY FORMATION |
|---|---|---|---|
| YELLOW NOVA | YELLOW | FLAT DAISY | TERMINAL 10 to 15 cm. PEDUNCLES |
| FLORIDA MARBLE | YELLOW TO LIGHT YELLOW | FLAT DAISY | TERMINAL AND COMPOUND 15 to 25 cm. PEDUNCLES |

| CULTIVAR | DIAMETER ACROSS FACE OF CAPITULUM | PLANT HEIGHT | FLOWER RESPONSE PERIOD |
|---|---|---|---|
| YELLOW NOVA | 75 to 90 mm. | TALL 75 to 90 cm. | 9 WEEKS |
| FLORIDA MARBLE | 70 to 105 mm. | TALL 75 to 85 cm. | 9 WEEKS |

COMPARISONS MADE OF PLANTS GROWN AS SINGLE STEM CUT SPRAYS WITH NO LONG DAYS IN SALINAS, CALIFORNIA

I claim:

1. A new and distinct plant of *Chrysanthemum morifolium,* Ramat., known by the cultivar name of Yellow Nova, as described and illustrated, and particularly characterized as to uniqueness by the combined characteristics of flat capitulum form; daisy capitulum type; yellow ray floret color; diameter across face of capitulum ranging from 75 to 95 mm. at maturity; uniform nine (9) week flowering response; tall plant height when grown as a single stem cut spray; 10 to 15 cm. peduncles on open, normally terminal sprays, and slow development of tight green discs, and tolerance of 13° C. (56° F.) for initiation and development when grown in single stem cut spray programs with a continuous dark period of 13 to 15 hours.

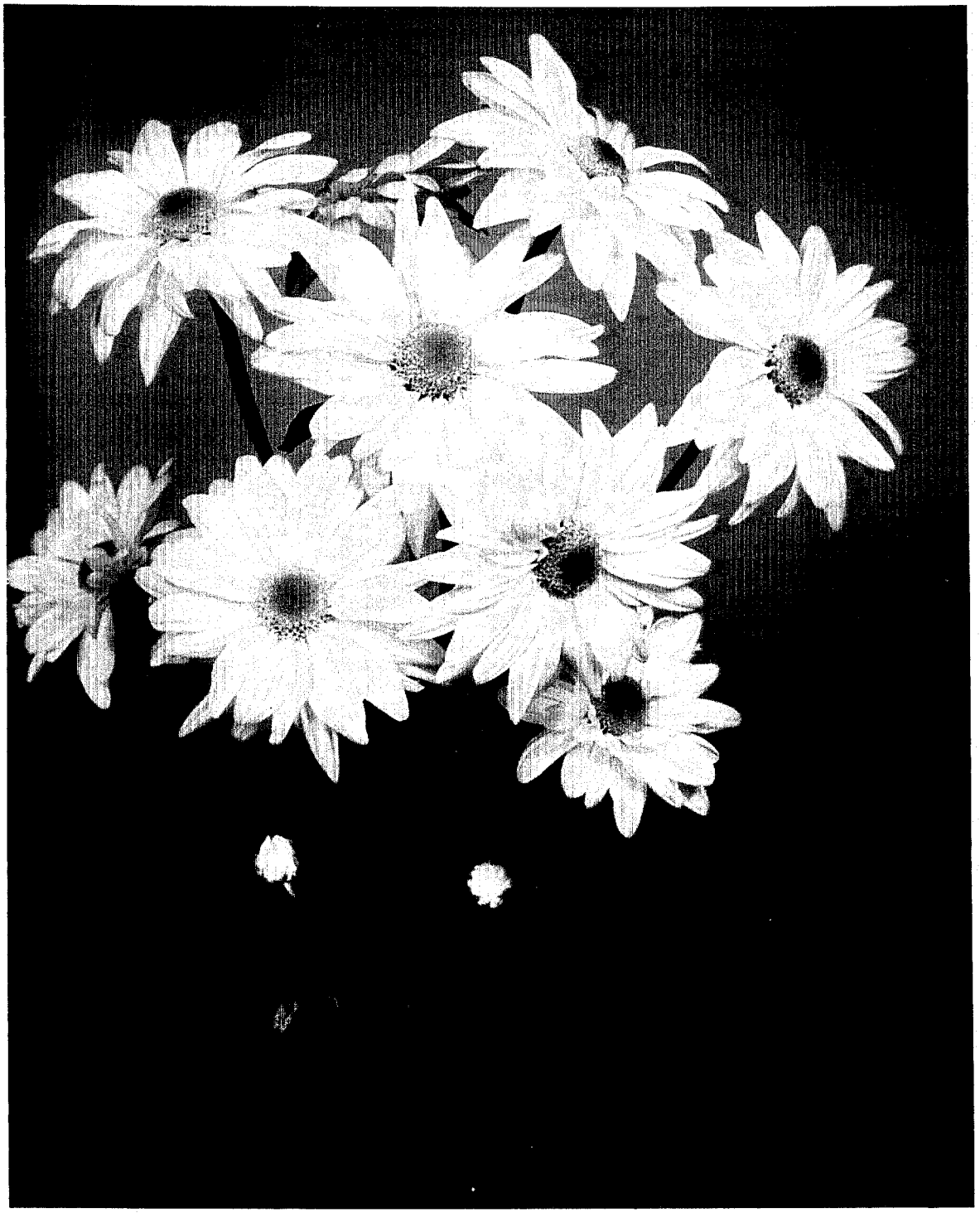

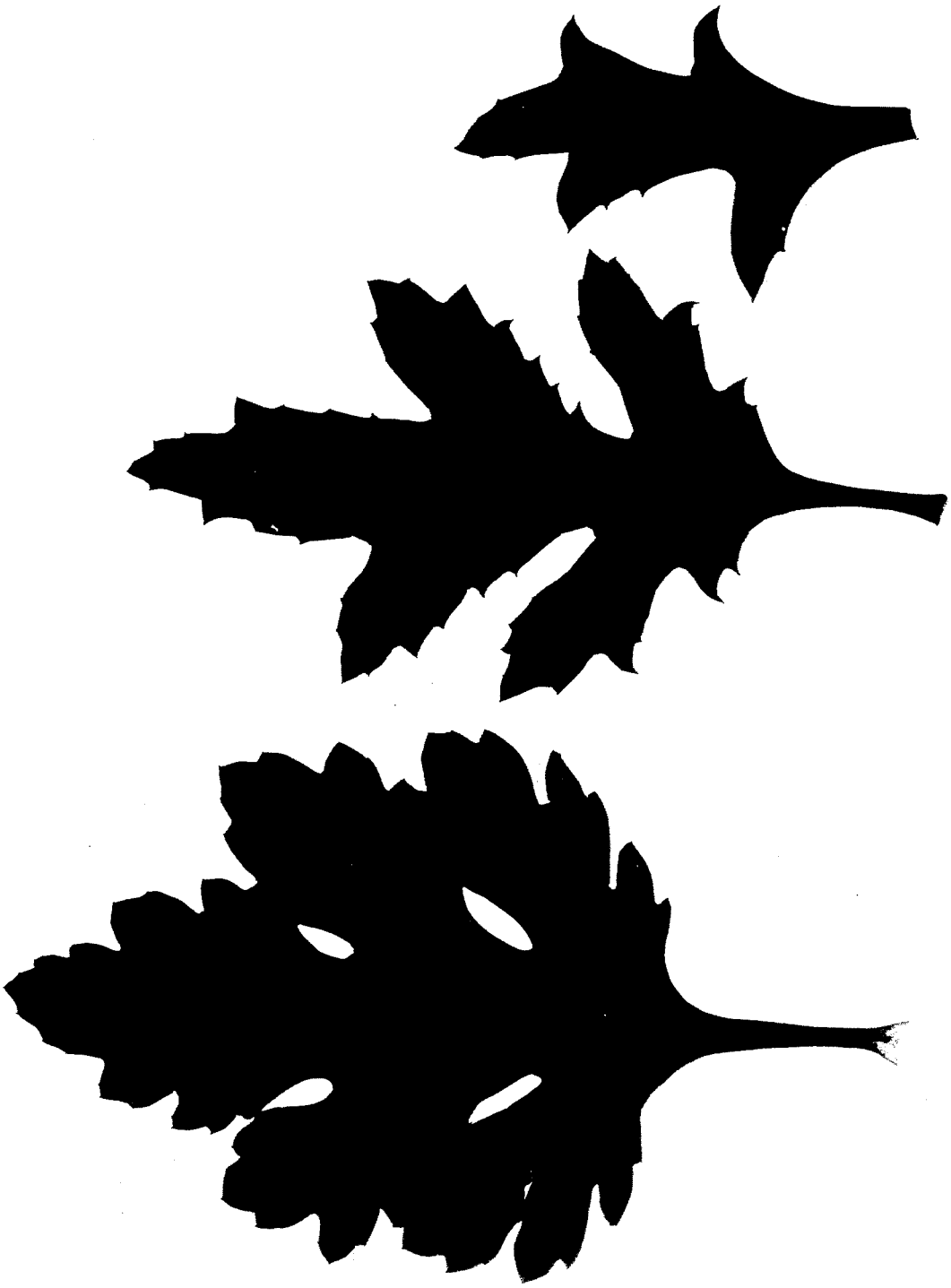

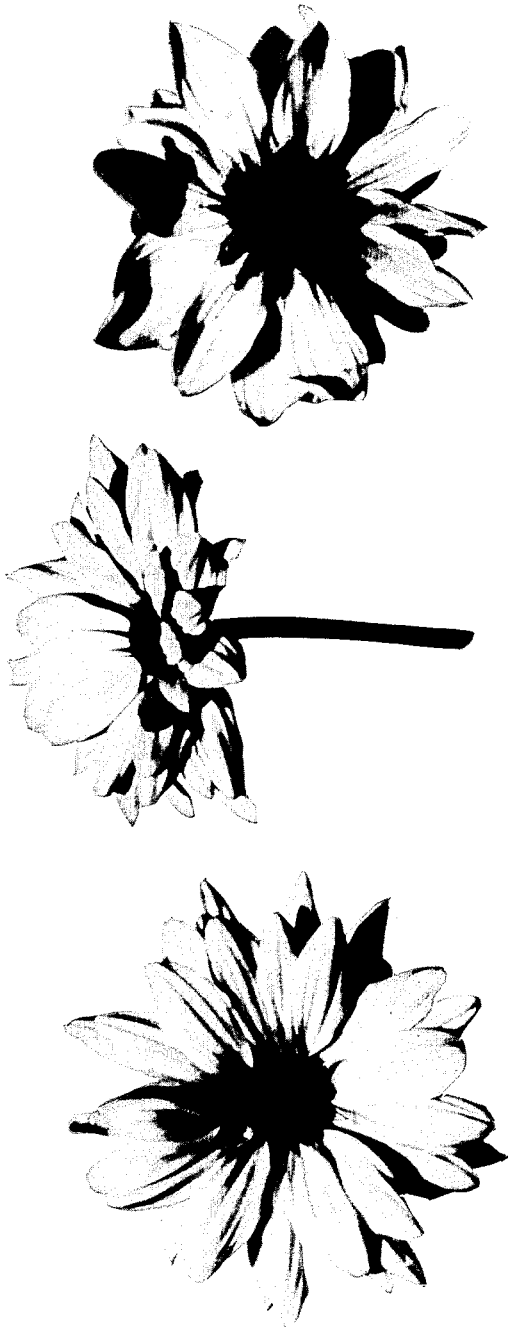

* * * * *